United States Patent [19]
Miffitt et al.

[11] Patent Number: 5,179,288
[45] Date of Patent: Jan. 12, 1993

[54] APPARATUS AND METHOD FOR MEASURING A BODILY CONSTITUENT

[75] Inventors: Donald Miffitt, Chelmsford, Mass.; Edward Poto, Somerville, N.J.; George Hovorka, Bedminster, N.J.; Arthur Costaris, Hampton, N.J.

[73] Assignee: Ortho Pharmaceutical Corporation, Raritan, N.J.

[21] Appl. No.: 769,031

[22] Filed: Sep. 30, 1991

[51] Int. Cl.$^5$ .................................................. G01N 33/16
[52] U.S. Cl. ..................................... 250/564; 128/633; 356/40
[58] Field of Search ................ 250/564, 565, 573, 574; 128/632, 633; 356/36, 39–42; 364/413.02, 413.07

[56] References Cited
U.S. PATENT DOCUMENTS

| | | | |
|---|---|---|---|
| 4,059,405 | 11/1977 | Sodickson et al. | 23/230 |
| 4,407,290 | 10/1983 | Wilber | 356/41 |
| 4,863,265 | 9/1989 | Flower et al. | 128/633 |
| 4,935,346 | 9/1990 | Phillips et al. | 435/14 |
| 5,059,394 | 10/1991 | Phillips et al. | 356/40 |

Primary Examiner—David C. Nelms
Assistant Examiner—S. Allen
Attorney, Agent, or Firm—Joel R. Petrow

[57] ABSTRACT

An apparatus and method for measuring a bodily constituent such as glucose or cholesterol by analyzing a sample taken from the body such as blood, saliva or urine. The sample is placed on a test strip inserted into the test block portion of the apparatus where the portion of the sample containing the constituent desired to be measured reacts with a chemical reagent. Products of this reaction have an absorbance/reflectance characteristic which is mathematically related to the concentration of the constituent in the bodily sample. The reflected light is absorbed by a photodiode and the output of the photodiode converted to a digital form where a microprocessor can calculate the concentration of the constituent using the mathematical relationship between the reflected light and concentration stored in memory means of the apparatus.

33 Claims, 2 Drawing Sheets

APPARATUS AND METHOD FOR MEASURING A BODILY CONSTITUENT

BACKGROUND OF INVENTION

It is not uncommon today for people under the burden of a medical condition to be able to manage their illness provided they have the capability to adequately monitor the status of their body.

In many cases the status that needs to be determined can be quantified through the measurement of a bodily constituent by taking a bodily sample, usually in the blood, although urine, saliva or even tissue samples may be used.

One example is the ability of diabetics to manage their condition, either with the use of insulin or strictly by diet, provided they can accurately and frequently quantify the level of glucose in their blood. While much effort in recent times has been devoted to providing diabetics with systems and methods for quickly and accurately measuring the glucose level in their blood, until now other bodily constituent measurements have been outside the province of the individual and require the offices of an institutional participant or medical professional in order to provide a sample and obtain a measurement.

One such health concern, albeit a long term one, is the level of cholesterol in the blood. It is well known that persons have a high level of blood cholesterol are more susceptible to various heart and circulatory ailments than those having a lower blood cholesterol level. Because blood cholesterol can be managed by a person through diet or medication, it is important for a person concerned about cholesterol level to be able to easily, frequently and accurately measure the concentration of cholesterol in his blood or other bodily sample indicative of the blood cholesterol level such as plasma, serum, saliva, urine or skin cholesterol in order to be able to take the appropriate actions to manage the condition.

Blood cholesterol level is one example of a bodily constituent, which is capable of being controlled by individual actions through diet, exercise and the like. It would be highly desirable if an individual could make easy, frequent, and accurate measurements of his blood cholesterol level.

U.S. Pat. No. 4,059,405 to Sodickson, et al., describes a method and apparatus for measuring constituents in a sample that generally requires reaction of the sample on a porous medium with reactants, illuminating the analysis site with electromagnetic radiation and measuring the radiation that is reflected therefrom. While generally utilizing reflectance measurements, a practical non-laboratory device is not taught.

U.S. Pat. No. 4,935,346 to Phillips, et al., describes a method and apparatus for determining the presence of an analyte in a fluid, particularly glucose in the blood. While effective, the device described in this patent requires the use of two light sources and complex, expensive 12 bit digital processing.

It is an object of the invention, therefore to provide an apparatus which is capable of being operated by an untrained individual and provides an accurate measurement of a desired bodily constituent.

It is a further object of the invention to provide an apparatus that requires a minimum number of steps on the part of the individual.

It is also an object of the invention to provide a device having the minimum number of components required to accomplish the objective of providing an easy, and accurate way to measure a bodily constituent level in order that the cost of the apparatus to the user is also minimized.

It is another object of the invention to provide an apparatus that is insensitive to the way in which the individual uses the device and does not require any calibration, timing or treatment of the sample used for the constituent measurement.

SUMMARY OF THE INVENTION

The above objects and others are achieved by an apparatus which requires the user only to insert a strip into the test block portion of the apparatus and place a small bodily sample on the chemical reagent strip. For instance, in measuring the cholesterol level in a sample of blood, a drop of blood is drawn. On the test strip, red blood cells are separated from the plasma portion of the blood sample by the use of two hydrophilic screening layers such as glycine treated paper and polycarbonate membrane. Red blood cells are trapped by both screening layers while the remainder of the blood passes on to react with a reagent reactive with cholesterol deposited on the reagent membrane. A test block includes a light emitting diode and a photodiode which receives light generated by the LED then reflected by blood reacted with the reagent. The LED is connected to a current source, controlled by a current regulator which controls the output of the LED by varying the current source value. The current through the photodiode, which is a function of the light reflected from the blood reacted with the reagent, has a mathematical relation to the concentration of the blood constituent that is being measured. This output is converted by an analog-to-digital convertor from an analog form to a digital form. The output of the analog-to-digital converter is provided to a microprocessor which also has access to electronic memory within the apparatus and can thereby calculate the concentration of the desired blood constituent by using the mathematical relation stored in the memory means and the digital input that is received. Finally, the microprocessor provides a digital electrical output of the calculated concentration of the blood constituent to a display, such as a liquid crystal display, which provides the output in a form understandable by the human user.

DESCRIPTION OF THE PREFERRED EMBODIMENT

While the description of the preferred embodiment will be directed toward the measurement of blood cholesterol, the invention is appropriate not only for measuring cholesterol in the blood but also for other bodily constituents which, when a bodily sample (such as blood, plasma, serum, saliva, urine or skin) is reacted with the appropriate reagent, yields absorbance/transmittance/reflectance in a portion of the electromagnetic spectrum that can be measured.

Construction of test strips and a detailed chemical description can be found in U.S. patent application Ser. No. 739,639 filed on Aug. 2, 1991, entitled "Device and Method For Conducting Biological Assays Containing Particulate Screening System" and assigned to the assignee of this application. A specific example is given as follows.

Figure 1:
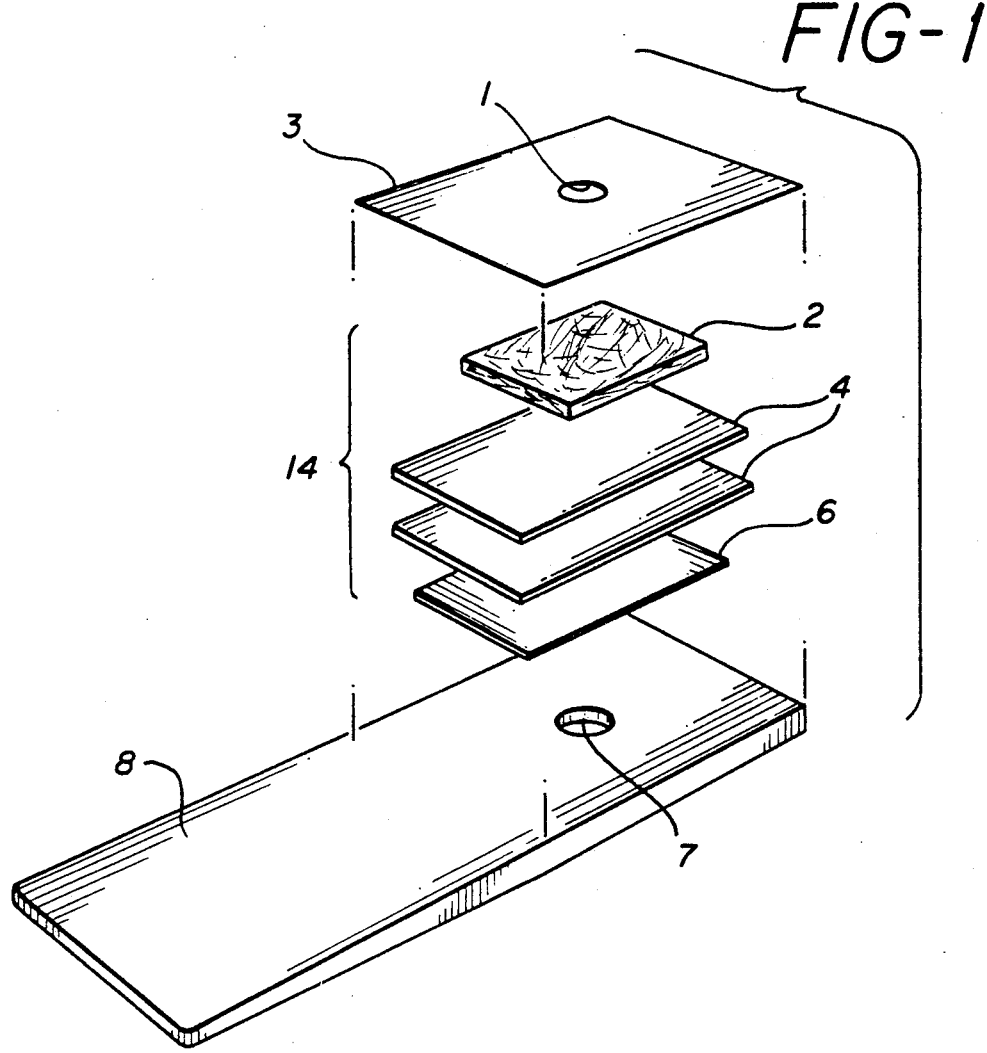
FIG. 1 is an exploded schematic of the test strip containing the reagent means upon which a sample of blood is placed.

With reference to FIG. 1, there is shown a test strip approximately 63.5 mm by 19 mm. The thickness of the strip is 0.33 mm at the handle end to about 1 mm where the reaction takes place. The strip has a blood application side containing a hole 1 which is approximately 4 mm in diameter and a reading side containing a hole 7 which is approximately 4.76 mm in diameter. Both holes are centered about 13 mm from the end.

The test strip further comprises a piece of plastic tape 3 which is 19×19 mm having one sticky side and containing the 4 mm hole 1. Beneath that is paper blood filter 2 such as Whatman 31 ET Chrom paper or Sigma's medium blotting paper. The paper is treated by coating the paper in a solution consisting of 1000 ml of water in which are dissolved 250 g of glycin, 5.5 g of sodium chloride, and 2.978 g disodium ethylenediaminetetraacetate (EDTA). The paper is coated by dipping into the solution and drying.

The next two layers beneath the paper blood filter are one or two polycarbonate membranes 4, such as Nucleopor's one micron polycarbonate membrane. This membrane is also coated with a solution made from 2 g of Triton X-100 dissolved in 1 liter of deionized water. The polycarbonate membrane is similarly dipped into the solution and dried.

The portion below the two polycarbonate membranes is the reagent membrane 6 containing a reagent reactive with cholesterol in the serum portion of the blood.

The membrane itself consists of a Pall Biosupport Biodyne B membrane, 8 microns in thickness. The reagent membrane is coated with two separate solutions: first, an organic solvent solution, then an aqueous solution. The organic solvent solution is 574.2 ml of methanol having added to it in the following sequence 50 g of Dioctyl sulfosuccinate sodium salt (DOSS), 21.54 g of Sodium Cholate, 250 ml of 0.2 molar 3, 3', 5, 5' tetramethylbenzidine (TMB) in DMSO.

The aqueous solution is made by mixing 400 ml of 5% Dextran % (w/v) with an average molecular weight of 5,000,000 to 40,000,000, 85.6 ml of 1.46 molar sucrose, 100 ml of 5% solution of Gantrez AN-139 polymer (available from GAF Chemical Company), 50 ml of 1 mol solution of sodium phosphate buffer, 1.0 M pH of 7.2, 100 ml of 10% solution of polyvinyl-pyrrollidone (PVP), 195,870 units Lipoprotein Lipase (LPL), 100,000 units of horseradish Peroxidase (POD), and 35,000 units of Cholesterol Oxidase. This solution is adjusted to a pH of 7.2 with sodium hydroxide or hydrocloric acid and water is added to obtain a final volume of 1,000 ml.

The reagent membrane is coated as follows: first by coating the Pall Biosupport Biodyne B membrane with organic solvent solution and then drying at an elevated temperature. The second coating, with the aqueous solution, is also followed by drying at elevated temperatures. The Pall Biodyne B membrane will now produce a color in proportion to the cholesterol content in bloods plasma. The final portion of the strip is the bottom portion containing hole 7 in plastic handle 8 upon which the above-described elements are placed as provided.

Figure 2:
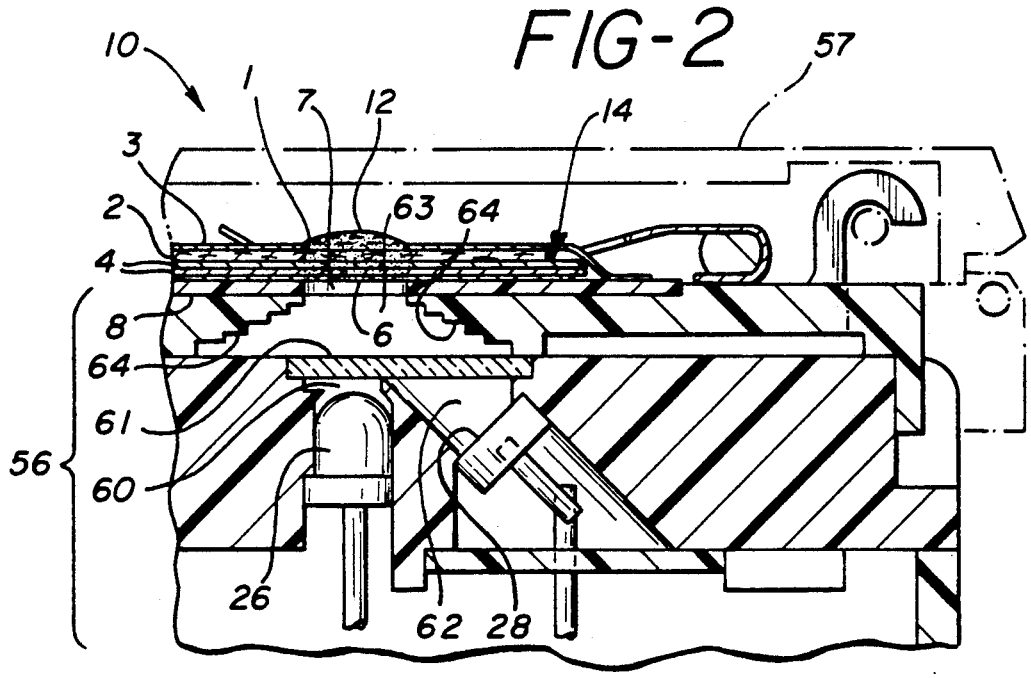
FIG. 2 is a cross sectional view of the test block assembly of the present invention.

Turning now to FIG. 2, shown is the test block 10 comprising a portion of the apparatus of the present invention. Common to that described above is a chemical reagents means 14 such as the reagent strip described above. On that strip is placed a portion of blood 12 only a small sample, typically one drop which is approximately 20 $\mu l$, is required. The strip is inserted into the test block portion of the apparatus (which in FIG. 2 would be into the plane of the paper), through an opening, and into a means for isolating the strip from external environmental influences such as the housing 56 and cover 57. This housing and cover serve primarily to block out extraneous electromagnetic radiation such as visible light.

The test block further comprises an emitter which is a source of electromagnetic radiation, such as light emitting diode (LED) 26. The LED must emit electromagnetic radiation such as visible light at a frequency wavelength in the electromagnet spectrum which is altered by the reaction of the blood constituent to be measured when it reacts with the reagent mean. In the case of the present example, that wavelength is 660 nanometers. The electromagnetic radiation such as visible light generated by LED 26 travels along a first passage 60 through a non-diffusive glass plate 61 and on to the reagent strip 14 where it impinges upon the chemical reagent reacted with the blood portion that has traveled to the reagent membrane. A receiver such as a photodiode 28 is disposed in a second passage 62 at an angle with the chemical reagent strip 14 that is substantially different from the angle of the first passage containing the LED. As can be seen from the Figure, the two passages 60 and 62 do not intersect and there is no direct path for light to travel from the LED through passage 60 to the second passage 62 and to the photodiode 28. Instead, the electromagnetic radiation such as light at 660 nanometers must travel along first passage 60, reflect off the chemical reagent strip and travel along second passage 62 and ultimately to the photodiode 28.

Further to this end of limiting the electromagnetic radiation received by the photodiode solely to that reflected by the reagent test strip, is the construction of chamber 63. Light received by the photodiode must exclude that emitted by the LED but not reflected by the chemical reagent strip. Chamber 63 is constructed by having a plurality of surfaces 64 disposed at individual angles to the first passage 60 such that any electromagnetic radiation from the LED emitter that passes through the non-diffusive glass plate 61 is reflected substantially away from the glass-plate 61 and not back toward the photodiode 28. In this sense chamber 63 with its surfaces 64 acts as a light trap. Another embodiment may be constructed of a flat, non-facetted but highly light absorbent, black surface.

Figure 3:
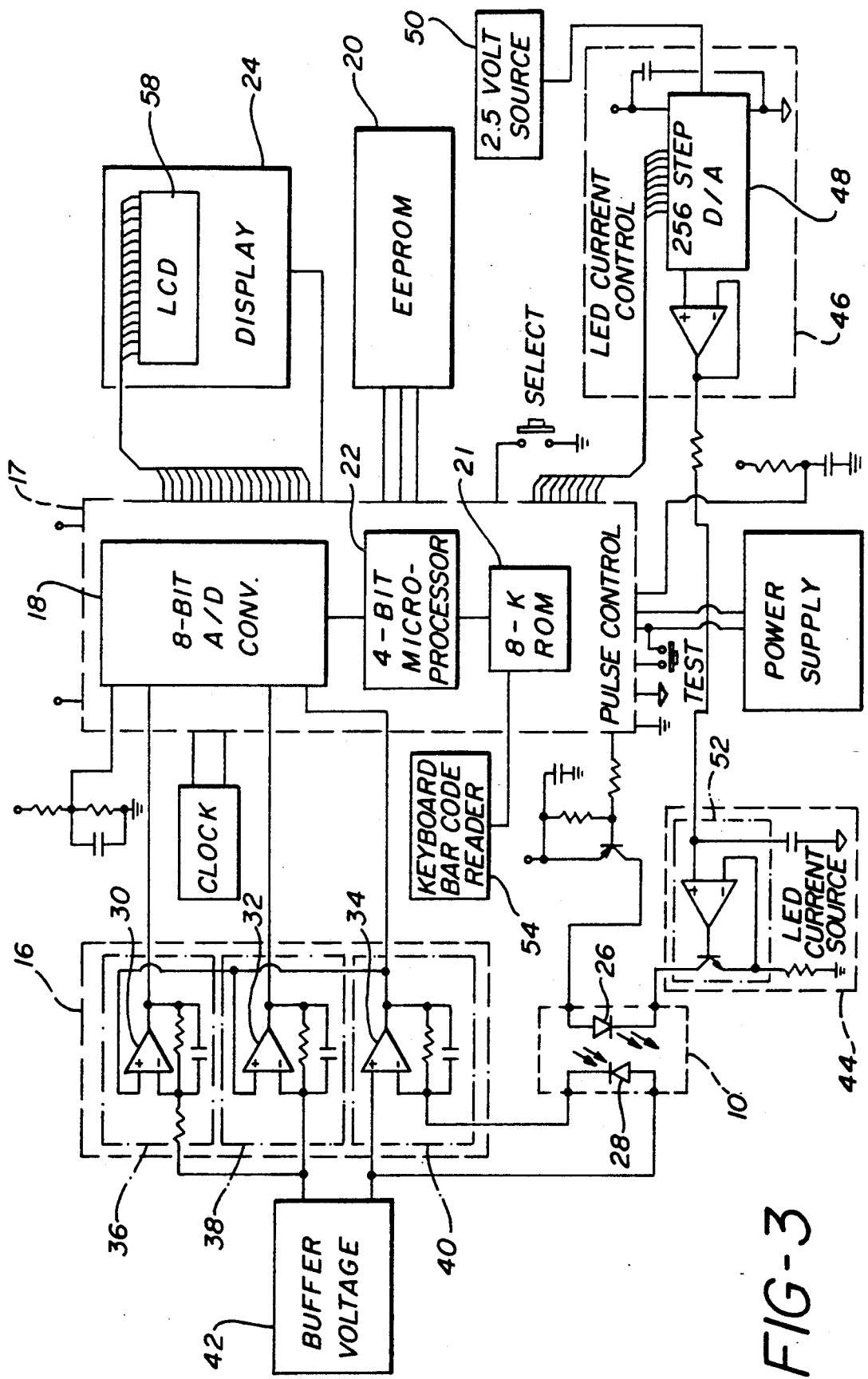
FIG. 3 is an electrical block diagram of the circuitry of the preferred embodiment of the present invention showing both discreet components and functional blocks.

Turning now to FIG. 3, shown is a schematic diagram of the circuitry of the apparatus of the present invention with certain functional blocks of the circuitry identified.

Consistent with that described above, test block 10 is shown containing LED 26 and photodiode 28. The current through photodiode 28 is provided to a plurality of electrical gain devices 16 such as the network of operational amplifiers 30, 32 and 34, which constitute a linear current-to-voltage circuit. These electrical gain devices apply three values of gain to the photodiode output. Operational amplifier 30 and its associated circuitry provide a gain of eight to the photodiode output; operational amplifier 32 and its associated circuitry provide a gain of four to the photodiode output and operational 34 and its associated circuitry provides unitary gain (i.e. a multiplier of one) to the photodiode output.

The output of the electrical gain devices 16 is then applied to a packaged electronic circuit or "chip" 17 such as model number 75328 from Nippon Electric Corporation (NEC) which contains among other circuits, an eight bit analog-to-digital converter 18. This analog-to-digital converter like all such converters, is capable of accepting a maximum analog input. If the analog input to the analog-to-digital converter exceeds the maximum, the digital output from the device 18 is not representative of the input, and will introduce errors into the digital calculation process.

On the other hand, when the analog input to the analog-to-digital converter is well below its maximum value the resolution that can be achieved is limited because digital bits remain unused and the analog value must be quantified with a small number of bits.

This limitation in general can be overcome by employing analog-to-digital converters that perform the digital quantization using a much larger number of bits than the 8 bit analog-to-digital converter used in the present example. This, however, runs counter to one of the primary objects of the invention which is to produce a blood constituent analyzer that is inexpensive yet accurate.

This apparent conflict between performance and cost is overcome by choosing the operational amplifier network output which is the largest of the set, but does not exceed the maximum analog input permitted to the analog-to-digital converter.

Therefore, with large analog signals a unitary gain 40 would be applied and the larger number could be converted to a digital format within the eight bit constraint of the converter using nearly the entire eight bit resolution. For lower analog signals, either the gain of four 38 or the gain of eight 36 would be selected, whichever is larger while remaining below the maximum allowable input. A concomitant increase in resolution would be achieved by substantially using all of the eight bit resolution of the analog digital converter 18.

Also associated with this embodiment are memory means such as electrically erasable programmable read only memory (EEPROM) 20 and in the case of the 75238 microprocessor 17, 8K of read only memory (ROM) 21 contained on the chip. Memory means may comprise means other than traditional data storage, such as a "hard-wired" representation of the mathematical relation between reflectance and constituent concentration. These memory means 20 and 21 contain information such as the mathematical relationship between the blood cholesterol level and the current of th photodiode which ultimately become a digital value from the A/D converter 18. Information such as the mathematical characterization would be contained in the nonvolatile memory of the ROM 21 contained on chip 17, whereas the EEPROM 20 would contain information that is particular to a single reading such as characterization information for the chemical reagent strip inserted into the reader for any particular test. Means for entering characterization values such as through a keyboard or bar code reader 54 would provide this characterization information to the EEPROM 20 that is necessary for subsequent calculations.

The digital output of the analog-to-digital converter 18 and information from memory means 20 and 21 are then provided to a 4 bit microprocessor also contained on the 75328 chip 17. For this particular chip a 4 bit microprocessor is utilized to calculate digitally the blood cholesterol level using characterization information from the EEPROM 20, the mathematical relationship stored in ROM 21 and the light reflectance value supplied in a digital form by A/D converter 18.

The microprocessor provides the results of its calculations to a display means such as liquid crystal display 58. This allows a presentation in a human understandable form of the calculated concentration of the blood constituent that is measured. In the case of a cholesterol measurement, the output would be in the range of 100-450 milligrams per deciliter.

The use of gain stages in combination with the 8 bit A/D converter provides an equivalent of higher resolution at lower signal levels, for example, by using a gain of 4 and a gain 8 in front of the A/D converter. When the signal is $\frac{1}{4}$ of the maximum input of A/D converter, the gain of 4 stage is added. This means that signals in this range still have 8 bits of resolution equivalent to a 10 bit A/D converter. When the signal is below $\frac{1}{8}$ full scale of the A/D converter, a gain of 8 can be used and the equivalent resolution is 11 bits. This approach is especially beneficial for the meter of the present invention because nearly all of the measurements fall below $\frac{1}{4}$ of the full scale, but on rare occasions extremes of strip characteristics, cholesterol level and ambient light levels can be accommodated.

In order that the selective electrical gain device 16 does not produce a voltage at or near 0 which may interfere with the appropriate calculations, a bias voltage may be applied by buffer 42. This voltage is summed with the output of the voltage multipliers 36, 38 and 40, in order that accuracy and linearity be maintained at low levels.

Power to the light emitting diode 26 is provided by current source 44 which causes the LED to emit electromagnetic radiation.

The current source 44 is connected to a current control means 46 which regulates the electromagnetic output of the light emitting diode by providing a number of different current source current values. The current source 44 is regulated by the current control means 46 so that the output of the LED 26 is within a predetermined range calculated by the microprocessor so that the electromagnetic radiation reflected by the chemical reagent means 14 reacted with the blood 12 and received by the photodiode 28 is within a range where the photodiode produces an electrical output having an accurate mathematical relation to the concentration of the blood constituent.

Control over the brightness of the LED 26 is exercised to assure adequate dynamic range of the photodetector sensor 28 across all required test conditions. The microprocessor 22 controls the light level by a digital output through the current control means 46 and LED current source 44. The current control means 46 in this embodiment utilizes a digital-to-analog converter 48 that receives an input from the microprocessor 22 and a voltage input from a fixed voltage source 50. The current control means 46 provides a voltage output converted to a current output by the current source, which in this embodiment utilizes a voltage to current converter circuit 52 to change the voltage input from the current control means 46 to a current source to power the LED 26.

This brightness circuit is required due to variations from LED to LED in manufacturing, changes in temperature, and aging of the LED. At the beginning of each test, if the reflectance does not fall within a predetermined voltage range, the digital-to-analog value is adjusted to bring the value to within a desired range.

Photometric data from the test block 10 is collected once per second in a sequence that is repeated every second as follows:

The LED is turned on. A period of 2 miliseconds is allowed to pass then a reading is taken with the LED on and in the next 16.6 milliseconds each photometric input is read 44 times for each of the gain levels 1, 4 and 8. The 44 readings for each gain level are added together and the LED is turned off for a period of 4 milliseconds. A reading is then taken with the LED off in order to determine electrical ambient light effects by reading each photometric input 44 times in 16.6 milliseconds. Again the 44 readings are added for each gain level. After this is completed, the electrical offset readings from the preceding procedure are subtracted from the readings taken with the LED on for each gain level. The resulting answer (i.e., with the electrical offset subtracted) is divided by 44 to get an average value. The LED remains off until the start of the next 1 second period.

When a user wishes to begin a test, the function is initiated by pressing a TEST button. If a strip has not been inserted, the reflectance of the testblock will be below a predetermined voltage level, in this embodiment 0.1 volts, and the LCD will prompt the user to "INSERT STRIP." When the dry chemical reagent strip is in place, and a steady voltage is measured (greater than the minimum expected strip voltage of 0.1 volts), the display then prompts the user to "ADD BLOOD." The unit will monitor reflectances off the strip continually once the dry strip is in place, thus detecting the application of a blood sample by an accompanying drop in reflectance. When the reflectance drops 5% or more relative to the initial voltage value, a sample is indicated as present and the word "TESTING" will be displayed. The test is then conducted and a result is displayed when the measured reflectance has reached a minimum value.

The voltage value at the highest resolution is selected from the values stored in each 1 second period. The criterion for selection is to evaluate the value from the stage of gain 1. If the value is less than 12.5% of the maximum analog input of the analog-to-digital converter, the voltage value from the stage of the gain of 8 is used; if not, but the value is less than 25% of maximum input of the analog-to-digital converter, then the stage with the gain of 4 voltage value is used. Otherwise, the voltage value of the stage having a gain of 1 is used.

When the value measured (adjusted for using the output of different stages of gain) changes less than a predetermined amount in a given period of time the apparatus stores that data as test end-point data. These values are then used to calculate the level of the blood constituent such as cholesterol. The calculational process utilizes 3 constants which are characterization parameters of the test strip and are placed into the memory of the apparatus. This is accomplished either by scrolling through a display and entering the appropriate values from a menu on the display with keyboard switches or reading the information directly off the test strip and into the memory using a bar code reader.

Entry of characterization parameters for a given test strip, which will be common to any given lot of test strips, may be accomplished by momentarily depressing the SELECT key. Each successive momentary depression of the SELECT key advances the display to present the next option to be specified. Means for changing a display option such as by pressing the TEST key allows the display to advance to the next option. Entry of a parameter is terminated by advancing through the entire sequence of parameters by successive depression of the SELECT key or by waiting for more than six seconds, when the meter automatically terminates parameter entry. In this way, the characterization parameters of the test strip which constitutes coefficients for the formula used to calculate the end numeral result are entered into the memory of the apparatus.

The internal workings of the apparatus are not apparent to the user. When the unit prompts the user to "INSERT STRIP" the user inserts the chemical reagent strip. When the unit prompts the user to "ADD BLOOD" the user opens the door, which acts as an isolation means from light and other electromagnetic radiation, and adds a drop of blood to the test strip which remains inserted in the meter.

The measurement block will reflect some light back to the photodetector even if no strip is in place at all. The amount of this reflection (Rblack) can be determined at the factory or immediately prior to each test and then stored to the non-volatile memory. Since Rblack voltage is proportional to the intensity of the LED light and since the actual test could be performed at a different light intensity, the Rblack value is ratioed as shown in the following formula:

$$\text{ratioed Rblack} = (\text{test light intensity/factory light intensity}) * \text{Rblack}.$$

The ratioed Rblack value is subtracted from every measurement to yield true reflection.

In the particular embodiment described herein for the calculation of blood cholesterol level, the formula for calculating the concentration of cholesterol in blood uses the three characterization parameters from the test strip and solves a second order equation.

After the number is calculated the result is displayed on a liquid crystal display or by other appropriate display means.

Error conditions which can be displayed as "TOO LOW" where the result is too low for the device to accurately measure, that is cholesterol is under 100 mg/dl; and "TOO HIGH" where the result is beyond the range of the apparatus that is cholesterol is above 400 mg/dl. In this instance the test is aborted because it would yield inaccurate results. In lower levels of ambient light, however, the resulting ambient light level is subtracted as described above and does not interfere with the test.

If the newly inserted test strip is too dark because of prolonged exposure to humidity or because blood was added to the strip before the strip was inserted in the meter, an error message will also be displayed.

Finally, an error will be displayed if the output voltage does not stabilize to within a predetermined range within three minutes.

What is claimed is:

1. An apparatus for measuring the concentration of a constituent in a bodily sample comprising:
   a test block adapted to receive said bodily sample and adapted to receive chemical reagent means reactive with the constituent desired to be measured, said test block producing an electrical output having a mathematical relation to the concentration of said constituent,
   a plurality of electrical gain devices operably connected to the test block to receive said test block electrical output,
   an analog-to-digital converter capable of accepting a maximum analog input, operably connected to the electrical output of said plurality of electrical gain devices, said electrical gain devices applying electrical gain to said test block output and said analog-to-digital converter selecting the largest device output which is less than the maximum acceptable analog input,
   memory means containing characterization information for said chemical reagent means and for said mathematical relation,
   a microprocessor operatively connected to the output of said analog-to-digital converter to receive the digital output of said converter and operatively connected to the memory means to read the contents of said memory means, said microprocessor adapted to calculate the concentration of said constituent, and
   a display means operably connected to said microprocessor to receive said calculated concentration of said constituent and display said concentration in human understandable form.

2. The apparatus of claim 1 wherein said test block comprises a light emitting diode adapted to expose said portion of constituent reacted with said chemical reagent means to electromagnetic radiation and a photodiode adapted to receive the electromagnetic radiation generated by the light emitting diode and reflected by said bodily sample reacted with said chemical reagent means and wherein said photodiode produces the electrical output having a mathematical relation to the concentration of said constituent.

3. The apparatus of claim 2 wherein said light emitting diode emits electromagnetic radiation in the visible light spectrum.

4. The apparatus of claim 1 wherein said bodily sample is a portion of blood.

5. The apparatus of claim 4 wherein said light emitting diode emits visible light of 660 nanometers.

6. The apparatus of claim 1 wherein said plurality of electrical gain devices comprises operational amplifiers.

7. The apparatus of claim 1 wherein said gain is set to be less than or equal to said maximum input of said analog-to-digital converter divided by the test block output.

8. The apparatus of claim 1 wherein a buffer is operatively connected to said selective electrical gain device, said buffer applying a voltage to said gain device in order that the output from said gain device to said microprocessor is always greater than zero and the output provided by the gain device to said microprocessor is the sum of the output of said gain device and the buffer voltage.

9. An apparatus for measuring the concentration of a constituent in a bodily sample comprising:
   a test block adapted to receive said bodily sample and adapted to receive chemical reagent means reactive with the constituent desired to be measured and producing an electrical output having a mathematical relation to the concentration of said constituent,
   said test block having a light emitting diode that radiates electromagnetic radiation onto said bodily sample reacted with said reagent means and a photodiode that receives electromagnetic radiation reflected from said constituent reacted with said reagent means,
   said light emitting diode operably connected to a current source, the current from said current source causing said light emitting diode to emit electromagnetic radiation,
   said current source operably connected to a current control means, said means regulating the electromagnetic output of said light emitting diode by providing a plurality of current source current values,
   said photodiode adapted to receive electromagnetic radiation emitted by said light emitting diode and reflected by said chemical reagent means reacted with said constituent, said photodiode producing said test block output having said mathematical relation to the concentration of said constituent,
   an analog-to-digital converter operably connected to said photodiode and producing a digital equivalent of said test block output,
   memory means containing characterization information for said chemical reagent means and for said mathematical relation,
   a microprocessor operatively connected to the output of said analog-to-digital converter to receive the digital output of said converter and operatively connected to the memory means to selectively read the contents of said memory means, said microprocessor adapted to calculate the concentration of said constituent, and
   a display means operably connected to said microprocessor to receive said calculated concentration of said constituent and display said concentration in human understandable form.

10. The apparatus of claim 9 wherein said light emitting diode radiates electromagnetic radiation in a visible light spectrum.

11. The apparatus of claim 9 wherein said microprocessor is operably connected to said current control means and said current source is regulated by said current control means such that the output of said light emitting diode is within a predetermined range calculated by said microprocessor so that the electromagnetic radiation reflected by said chemical reagent means reacted with said constituent and received by said photodiode is within a range that the photodiode produces an electrical output having an accurate mathematical relation to the concentration of said constituent.

12. The apparatus of claim 9 wherein said current control means comprises a digital-to-analog converter receiving an input from said microprocessor and receiving a further input from a fixed voltage source, said current control means having an output which is one of a plurality of voltage values.

13. The apparatus of claim 12 wherein said current source comprises a voltage to current converter circuit which receives a voltage input from the output of said current control means.

14. The apparatus of claim 9 wherein said bodily sample is blood.

15. The apparatus of claim 14 wherein said constituent in the blood is cholesterol.

16. A apparatus for self-testing to determine the concentration of cholesterol comprising:
a test block adapted to receive a bodily sample containing cholesterol and adapted to receive chemical reagent means reactive with cholesterol,
means for entering into said apparatus a characterization value associated with said reactive chemical reagent means,
an emitter and a receiver which comprise a portion of said test block, the output of said emitter impinging on the reagent means reacted with cholesterol and said receiver receiving a portion of the output after the output has interacted with the reagent means reacted with cholesterol,
means for isolating said bodily sample, said reagent means and said receiver contained within said test block from extraneous environmental noise and contaminants,
a microprocessor electrically connected to said receiver and in communication with the characterization value entered into said apparatus, adapted to calculate the concentration of cholesterol in the bodily sample deposited in the apparatus, and
a display for presenting said calculated concentration of cholesterol in a human understandable form.

17. The apparatus of claim 16 wherein said bodily sample is a portion of blood.

18. The apparatus of claim 16 wherein said chemical reagent means reactive with cholesterol comprises a test strip coated with a chemical reagent and adapted to be inserted into the test block portion of said device.

19. The apparatus of claim 16 wherein said means for entering into said device a characterization value comprises means for scrolling a menu of values on said display means and a means for entering one such value into the device.

20. The apparatus of claim 16 wherein said means for entering into said device a characterization value comprises a bar code on said chemical reagent means and a bar code reader comprising a portion of said apparatus.

21. The apparatus of claim 16 wherein said emitter is a light emitting diode.

22. The apparatus of claim 16 wherein said receiver is a photodiode.

23. The apparatus of claim 17 wherein said portion of the output of the light emitting diode received by the photodiode after having interacted with the reagent means reacted with said blood portion is reflected light.

24. The apparatus of claim 22 wherein said microprocessor is electrically connected to said photodiode by having the current output of said photodiode pass through a current to voltage converter, the voltage of which provides an input to said microprocessor.

25. A method for measuring the concentration of a constituent in a bodily sample comprising:
taking said bodily sample and reacting said sample with a chemical reagent reactive with the constituent desired to be measured,
producing an electrical output having a mathematical relation to the concentration of said constituent,
producing a plurality of voltage values each of which is a multiple of the voltage associated with said electrical output of the test block,
providing the plurality of voltages to an analog-to-digital converter,
selecting for digital processing the largest voltage of the plurality which is less than or equal to the maximum input voltage of the analog-to-digital converter,
providing the digital output of the analog-to-digital converter to a microprocessor which can address a memory means containing characterization information for said chemical reagent means,
calculating in said microprocessor the concentration of said constituent from the digital form of the test block electrical output and the characterization information for said chemical reagent means, and
displaying the calculated concentration of said constituent in human understandable form on a visible display output.

26. A method for measuring the concentration of a bodily constituent comprising:
storing in a memory device characterization information defining a mathematical relationship between the concentration of said constituent and electromagnetic radiation reflected by a chemical reagent means reacted with said constituent,
receiving in a test block a bodily sample and said chemical reagent means reactive with the constituent desired to be measured in the bodily sample,
producing electromagnetic radiation and directing it to impinge upon said constituent reacted with said reagent means,
measuring electromagnetic radiation reflected from said sample reacted with said reagent means,
producing an analog electrical output from said electromagnetic radiation reflected from said constituent reacted with said reagent means, said analog electrical output having said mathematical relationship to the concentration of said constituent,
converting said analog electrical output to a digital equivalent, controlling the amount of electromagnetic radiation impinging upon said constituent reacted with said reagent means by controlling the power provided to the source of said electromagnetic radiation to produce an analog electrical output within a predetermined range,
electronically calculating the concentration of said constituent by using the mathematical relation of the digital equivalent of the electrical output of the test block to the concentration of said constituent, and
displaying said calculated concentration of constituent in human understandable form.

27. The method of claim 26 comprising the additional steps of:
measuring the ambient electromagnetic radiation within said test block when no electromagnetic radiation is produced,
converting an analog output from such measurement into a digital value,
subtracting said ambient digital value from said digital equivalent of radiation reflected generated by impinging with electromagnetic radiation, and
performing said calculation of said constituent concentration.

28. An apparatus for measuring the concentration of a bodily constituent comprising:
a test block adapted to receive a bodily sample and adapted to receive a chemical reagent strip reactive with the constituent desired to be measured and producing an electrical output having a mathematical relation to the concentration of said constituent, said test block having an emitter that radiates electromagnetic radiation onto said constituent reacted with said reagent strip and a receiver that receives electromagnetic radiation reflected from said constituent reacted with said reagent strip, said test block having separate, non-intersecting passages in said test block, a first passage containing the emitter and terminating at said chemical reagent strip and a second passage containing the receiver and terminating at said chemical reagent strip, said passages forming substantially different angles with respect to the surface of the chemical reagent strip, said test block further having a chamber with a plurality of surfaces, said surfaces disposed at individual angles to said chemical reagent strip such that electromagnetic radiation from said emitter passing through said chemical reagent strip is reflected substantially away from said chemical reagent strip, said emitter operably connected to a current source, the current from said current source causing said emitter to emit electromagnetic radiation, said receiver adapted to receive electromagnetic radiation emitted by said emitter and reflected by said chemical reagent strip reacted with said constituent, said receiver producing said test block output having said mathematical relation to the concentration of said constituent, an analog-to-digital converter operably connected to said receiver and producing a digital equivalent of said test block output, memory means containing said mathematical relation, a microprocessor operatively connected to the output of said analog-to-digital converter to receive the digital output of said converter and operatively connected to the memory means to selectively read the contents of said memory means, said microprocessor adapted to calculate the concentration of said constituent, and a display means operably connected to said microprocessor to receive said calculated concentration of said constituent and display said concentration in human understandable form.

29. The apparatus of claim 28 wherein said bodily sample is blood.

30. The apparatus of claim 28 wherein said constituent is cholesterol.

31. The apparatus of claim 28 wherein said emitter is a light emitting diode.

32. The apparatus of claim 28 wherein said receiver is a photodiode.

33. The apparatus of claim 31 wherein said current source is operably connected to a current control means, said means regulating the electromagnetic output of said light emitting diode by providing a plurality of current source values.

* * * * *